(12) United States Patent
Nikolskiy et al.

(10) Patent No.: US 11,559,378 B2
(45) Date of Patent: Jan. 24, 2023

(54) SCANNING DENTAL IMPRESSIONS

(71) Applicant: James R. Glidewell Dental Ceramics, Inc., Newport Beach, CA (US)

(72) Inventors: Sergey Nikolskiy, Coto De Caza, CA (US); David Christopher Leeson, North Tustin, CA (US); Shih-Kai Lai, Irvine, CA (US); Loraine Allessandra Queji Silva, Huntington Beach, CA (US)

(73) Assignee: James R. Glidewell Dental Ceramics, Inc., Newport Beach, CA (US)

( * ) Notice: Subject to any disclaimer, the term of this patent is extended or adjusted under 35 U.S.C. 154(b) by 695 days.

(21) Appl. No.: 15/816,120

(22) Filed: Nov. 17, 2017

(65) Prior Publication Data

US 2018/0132982 A1   May 17, 2018

Related U.S. Application Data

(60) Provisional application No. 62/423,460, filed on Nov. 17, 2016.

(51) Int. Cl.
*A61C 13/00* (2006.01)
*A61C 9/00* (2006.01)
(Continued)

(52) U.S. Cl.
CPC ........ *A61C 13/0004* (2013.01); *A61C 9/0006* (2013.01); *A61C 9/0046* (2013.01); *A61C 19/05* (2013.01); *G06F 30/00* (2020.01); *G06T 7/0012* (2013.01); *G06T 17/00* (2013.01); *A61B 6/032* (2013.01); *A61B 6/14* (2013.01);
*G06T 2207/10028* (2013.01); *G06T 2207/10081* (2013.01); *G06T 2207/30036* (2013.01); *G06T 2210/41* (2013.01)

(58) Field of Classification Search
CPC . A61C 13/0004; A61C 9/0006; A61C 9/0046; A61C 19/05; G06F 30/00; G06T 7/0012; G06T 17/00; G06T 2207/10028; G06T 2207/10081; G06T 2207/30036; G06T 2210/41; A61B 6/032; A61B 6/14
See application file for complete search history.

(56) References Cited

U.S. PATENT DOCUMENTS

| D302,683 S | 8/1989 | Iwasaki et al. |
| 5,023,895 A | 6/1991 | McCroskey et al. |

(Continued)

FOREIGN PATENT DOCUMENTS

| CN | 108024841 A | 5/2018 |
| CN | 108665533 A | 10/2018 |

(Continued)

OTHER PUBLICATIONS

Hollt et al, "GPU-Based Direct vol. Rendering of Industrial CT Data" (Year: 2007).*

(Continued)

*Primary Examiner* — John E Johansen
(74) *Attorney, Agent, or Firm* — Charles Fowler

(57) ABSTRACT

Systems and methods are provided for scanning a dental impression to obtain a digital model of a patient's dentition as an input to computer aided design (CAD) and computer aided manufacturing (CAM) methods for producing dental prostheses.

10 Claims, 6 Drawing Sheets

(51) Int. Cl.
  *G06T 7/00* (2017.01)
  *A61C 19/05* (2006.01)
  *A61B 6/14* (2006.01)
  *A61B 6/03* (2006.01)
  *G06T 17/00* (2006.01)
  *G06F 30/00* (2020.01)

(56) References Cited

U.S. PATENT DOCUMENTS

| | | | |
|---|---|---|---|
| 5,270,827 A | 12/1993 | Kobyayashi et al. | |
| 5,368,478 A | 11/1994 | Andreiko et al. | |
| 5,431,562 A | 7/1995 | Andreiko et al. | |
| 5,447,432 A | 9/1995 | Andreiko et al. | |
| 5,454,717 A | 10/1995 | Andreiko et al. | |
| 5,605,459 A | 2/1997 | Kuroda et al. | |
| D394,316 S | 5/1998 | Kodama et al. | |
| 5,879,158 A | 3/1999 | Doyle et al. | |
| 6,068,482 A | 5/2000 | Snow | |
| 6,081,739 A | 6/2000 | Lemchen | |
| 6,091,412 A | 7/2000 | Simonoff et al. | |
| 6,152,731 A | 11/2000 | Jordan et al. | |
| 6,198,552 B1 | 3/2001 | Nagae | |
| 6,217,334 B1 | 4/2001 | Hultgren | |
| 6,227,850 B1 | 5/2001 | Chishti et al. | |
| 6,244,861 B1 | 6/2001 | Andreiko et al. | |
| 6,318,994 B1 | 11/2001 | Chishti et al. | |
| 6,322,359 B1 | 11/2001 | Jordan et al. | |
| 6,350,120 B1 | 2/2002 | Sachdeva et al. | |
| 6,371,761 B1 | 4/2002 | Cheang et al. | |
| 6,386,867 B1 | 5/2002 | Durbin et al. | |
| 6,386,878 B1 | 5/2002 | Pavlovskaia et al. | |
| 6,406,292 B1 | 6/2002 | Chishti et al. | |
| 6,409,504 B1 | 6/2002 | Jones et al. | |
| 6,450,807 B1 | 9/2002 | Chishti et al. | |
| 6,463,344 B1 | 10/2002 | Pavloskaia et al. | |
| 6,512,994 B1 | 1/2003 | Sachdeva | |
| 6,554,611 B2 | 4/2003 | Chishti et al. | |
| 6,582,225 B1 | 6/2003 | Bergersen | |
| D476,658 S | 7/2003 | Machi et al. | |
| 6,602,070 B2 | 8/2003 | Miller et al. | |
| 6,621,491 B1 | 9/2003 | Baumrind et al. | |
| 6,632,089 B2 | 10/2003 | Rubbert et al. | |
| 6,633,789 B1 | 10/2003 | Nikolskiy et al. | |
| 6,648,640 B2 | 11/2003 | Rubbert et al. | |
| 6,688,886 B2 | 2/2004 | Hughes et al. | |
| 6,726,478 B1 | 4/2004 | Isiderio et al. | |
| 6,767,208 B2 | 7/2004 | Kaza | |
| 6,783,360 B2 | 8/2004 | Chishti | |
| 7,013,191 B2 | 3/2006 | Rubbert et al. | |
| 7,027,642 B2 | 4/2006 | Rubbert et al. | |
| 7,029,275 B2 | 4/2006 | Rubbert et al. | |
| 7,040,896 B2 | 5/2006 | Pavlovskaia et al. | |
| 7,068,825 B2 | 6/2006 | Rubbert et al. | |
| 7,080,979 B2 | 7/2006 | Rubbert et al. | |
| 7,134,874 B2 | 11/2006 | Chishti et al. | |
| 7,140,877 B2 | 11/2006 | Kaza | |
| D533,555 S | 12/2006 | Odhe et al. | |
| 7,156,655 B2 | 1/2007 | Sachdeva et al. | |
| 7,234,937 B2 | 6/2007 | Sachdeva et al. | |
| 7,292,716 B2 | 11/2007 | Kim | |
| 7,361,018 B2 | 4/2008 | Imgrund et al. | |
| 7,361,020 B2 | 4/2008 | Abolfathi et al. | |
| 7,373,286 B2 | 5/2008 | Nikolskiy et al. | |
| D573,146 S | 7/2008 | Sukenari et al. | |
| D580,962 S | 11/2008 | Sukenari et al. | |
| 7,476,100 B2 | 1/2009 | Kuo | |
| 7,545,372 B2 | 6/2009 | Kopelman et al. | |
| 7,609,875 B2 | 10/2009 | Liu et al. | |
| D612,851 S | 3/2010 | Maruyama et al. | |
| 7,717,708 B2 | 5/2010 | Sachdeva et al. | |
| 7,740,476 B2 | 6/2010 | Rubbert et al. | |
| 7,805,003 B1 | 9/2010 | Cohen et al. | |
| 8,013,853 B1 | 9/2011 | Douglas et al. | |
| 8,045,180 B2 | 10/2011 | Friemel | |
| 8,075,306 B2 | 12/2011 | Kitching et al. | |
| 8,229,180 B2 | 7/2012 | Baloch et al. | |
| 8,308,481 B2 | 11/2012 | DiAngelo et al. | |
| 8,332,061 B2 | 12/2012 | Baloch et al. | |
| 8,342,843 B2 | 1/2013 | Perot et al. | |
| 8,380,644 B2 | 2/2013 | Zouhar et al. | |
| D678,383 S | 3/2013 | Park et al. | |
| D714,940 S | 10/2014 | Kim | |
| 8,855,375 B2 | 10/2014 | Macciola et al. | |
| 8,995,732 B2 | 3/2015 | Kaza et al. | |
| 9,055,988 B2 | 6/2015 | Galgut et al. | |
| 9,135,498 B2 | 9/2015 | Andreiko et al. | |
| D742,010 S | 10/2015 | Metcalf | |
| 9,421,074 B2 | 8/2016 | Sachdeva et al. | |
| D776,818 S | 1/2017 | Metcalf | |
| 9,629,698 B2 | 4/2017 | Lior et al. | |
| 9,737,381 B2 | 8/2017 | Lee | |
| 9,888,983 B2 | 2/2018 | Sachdeva et al. | |
| 10,149,744 B2 | 12/2018 | Lior et al. | |
| 10,624,717 B2 | 4/2020 | Wen | |
| 2002/0006217 A1 | 1/2002 | Rubbert et al. | |
| 2002/0028418 A1 | 3/2002 | Farag et al. | |
| 2002/0141626 A1 | 10/2002 | Caspi | |
| 2002/0150859 A1 | 10/2002 | Imgrund et al. | |
| 2003/0198377 A1 | 10/2003 | Ng | |
| 2003/0198378 A1 | 10/2003 | Ng | |
| 2003/0207227 A1 | 11/2003 | Abolfathi | |
| 2003/0207235 A1 | 11/2003 | Van der Zel | |
| 2003/0224314 A1 | 12/2003 | Bergersen | |
| 2004/0072120 A1 | 4/2004 | Lauren | |
| 2004/0146198 A1 | 7/2004 | Herley | |
| 2004/0152036 A1 | 8/2004 | Abolfathi | |
| 2004/0175671 A1 | 9/2004 | Jones et al. | |
| 2004/0197728 A1 | 10/2004 | Abolfathi et al. | |
| 2004/0214128 A1 | 10/2004 | Sachdeva et al. | |
| 2005/0018901 A1 | 1/2005 | Kaufmann et al. | |
| 2005/0019732 A1 | 1/2005 | Kaufmann et al. | |
| 2005/0030368 A1 | 2/2005 | Morrison | |
| 2005/0043837 A1 | 2/2005 | Rubbert et al. | |
| 2005/0089213 A1 | 4/2005 | Geng | |
| 2005/0089822 A1* | 4/2005 | Geng | A61C 13/0004 433/215 |
| 2005/0191593 A1 | 9/2005 | Knopp | |
| 2005/0192835 A1 | 9/2005 | Kuo et al. | |
| 2005/0208449 A1 | 9/2005 | Abolfathi et al. | |
| 2005/0271996 A1 | 12/2005 | Sporbert et al. | |
| 2006/0127859 A1 | 6/2006 | Wen | |
| 2006/0147872 A1 | 7/2006 | Andreiko | |
| 2006/0154198 A1* | 7/2006 | Durbin | A61C 9/0053 433/29 |
| 2006/0263739 A1 | 11/2006 | Sporbert et al. | |
| 2006/0263741 A1 | 11/2006 | Imgrund et al. | |
| 2006/0275736 A1 | 12/2006 | Wen et al. | |
| 2007/0003900 A1 | 1/2007 | Miller | |
| 2007/0031790 A1 | 2/2007 | Raby et al. | |
| 2007/0031791 A1 | 2/2007 | Cinader et al. | |
| 2007/0065768 A1 | 3/2007 | Nadav | |
| 2007/0128573 A1 | 6/2007 | Kuo | |
| 2007/0128574 A1 | 6/2007 | Kuo et al. | |
| 2007/0129991 A1 | 6/2007 | Kuo | |
| 2007/0134613 A1 | 6/2007 | Kuo et al. | |
| 2007/0141527 A1 | 6/2007 | Kuo et al. | |
| 2007/0167784 A1 | 7/2007 | Shekhar et al. | |
| 2007/0168152 A1 | 7/2007 | Matov et al. | |
| 2007/0190481 A1 | 8/2007 | Schmitt | |
| 2007/0207441 A1 | 9/2007 | Lauren | |
| 2007/0238065 A1 | 10/2007 | Sherwood et al. | |
| 2008/0020350 A1 | 1/2008 | Matov et al. | |
| 2008/0048979 A1 | 2/2008 | Ruttenberg | |
| 2008/0057466 A1 | 3/2008 | Jordan et al. | |
| 2008/0064008 A1 | 3/2008 | Schmitt | |
| 2008/0182220 A1 | 7/2008 | Chishti et al. | |
| 2008/0248443 A1 | 10/2008 | Chishti et al. | |
| 2008/0261165 A1 | 10/2008 | Steingart et al. | |
| 2008/0305458 A1 | 12/2008 | Lemchen | |
| 2009/0080746 A1 | 3/2009 | Ku et al. | |
| 2009/0087817 A1 | 4/2009 | Jansen et al. | |
| 2009/0162813 A1 | 6/2009 | Glor et al. | |
| 2009/0191503 A1 | 7/2009 | Matov et al. | |

(56) References Cited

U.S. PATENT DOCUMENTS

| | | | |
|---|---|---|---|
| 2009/0220916 A1* | 9/2009 | Fisker | A61B 5/055 433/201.1 |
| 2009/0246726 A1 | 10/2009 | Chelnokov et al. | |
| 2009/0248184 A1* | 10/2009 | Steingart | G06F 3/016 700/98 |
| 2009/0298017 A1 | 12/2009 | Boerjes et al. | |
| 2009/0311647 A1 | 12/2009 | Fang et al. | |
| 2010/0009308 A1 | 1/2010 | Wen | |
| 2010/0100362 A1 | 4/2010 | Zouhar et al. | |
| 2010/0105009 A1* | 4/2010 | Karkar | A61C 1/084 433/215 |
| 2010/0111386 A1 | 5/2010 | El-Baz | |
| 2010/0138025 A1 | 6/2010 | Morton et al. | |
| 2010/0145898 A1 | 6/2010 | Malfliet et al. | |
| 2010/0217567 A1 | 8/2010 | Marshall | |
| 2010/0260405 A1 | 10/2010 | Cinader, Jr. | |
| 2010/0297572 A1 | 11/2010 | Kim | |
| 2011/0004331 A1 | 1/2011 | Cinader, Jr. et al. | |
| 2011/0045428 A1 | 2/2011 | Boltunov et al. | |
| 2011/0059413 A1 | 3/2011 | Schutyser et al. | |
| 2011/0060438 A1 | 3/2011 | Stoddard et al. | |
| 2011/0090513 A1 | 4/2011 | Seidl et al. | |
| 2011/0184762 A1 | 7/2011 | Chishti et al. | |
| 2011/0206247 A1 | 8/2011 | Dachille et al. | |
| 2011/0207072 A1 | 8/2011 | Schiemann | |
| 2011/0244415 A1 | 10/2011 | Batesole | |
| 2011/0268326 A1 | 11/2011 | Kuo et al. | |
| 2011/0292047 A1 | 12/2011 | Chang et al. | |
| 2012/0015316 A1 | 1/2012 | Sachdeva et al. | |
| 2012/0065756 A1* | 3/2012 | Rubbert | A61C 8/0048 700/98 |
| 2012/0088208 A1 | 4/2012 | Schulter et al. | |
| 2012/0139142 A1 | 6/2012 | Van der Zel | |
| 2012/0214121 A1 | 8/2012 | Greenberg | |
| 2013/0172731 A1* | 7/2013 | Gole | A61B 5/7425 600/424 |
| 2013/0218531 A1 | 8/2013 | Deichmann et al. | |
| 2013/0226534 A1 | 8/2013 | Fisker et al. | |
| 2013/0275107 A1 | 10/2013 | Alpern et al. | |
| 2013/0325431 A1 | 12/2013 | See et al. | |
| 2013/0329020 A1 | 12/2013 | Krivechko et al. | |
| 2013/0335417 A1 | 12/2013 | McQueston et al. | |
| 2014/0003695 A1* | 1/2014 | Dean | G06T 7/001 382/131 |
| 2014/0055135 A1 | 2/2014 | Nielsen et al. | |
| 2014/0067334 A1 | 3/2014 | Kuo | |
| 2014/0067337 A1 | 3/2014 | Kopleman | |
| 2014/0185742 A1* | 7/2014 | Chen | G06T 7/187 378/5 |
| 2014/0272772 A1 | 9/2014 | Andreiko et al. | |
| 2014/0278278 A1 | 9/2014 | Nikolskiy et al. | |
| 2014/0278279 A1 | 9/2014 | Azernikov et al. | |
| 2014/0308624 A1 | 10/2014 | Lee et al. | |
| 2014/0329194 A1 | 11/2014 | Sachdeva et al. | |
| 2014/0379356 A1 | 12/2014 | Sachdeva et al. | |
| 2015/0049081 A1 | 2/2015 | Coffey et al. | |
| 2015/0056576 A1 | 2/2015 | Nikolskiy et al. | |
| 2015/0111168 A1 | 4/2015 | Vogel | |
| 2015/0154678 A1 | 6/2015 | Fonte et al. | |
| 2015/0182316 A1* | 7/2015 | Morales | A61C 13/01 433/199.1 |
| 2015/0320320 A1 | 11/2015 | Kopelman et al. | |
| 2015/0347682 A1 | 12/2015 | Chen et al. | |
| 2016/0135924 A1 | 5/2016 | Choi et al. | |
| 2016/0148370 A1 | 5/2016 | Maury et al. | |
| 2016/0239631 A1 | 8/2016 | Wu et al. | |
| 2016/0256035 A1 | 8/2016 | Kopelman et al. | |
| 2016/0256246 A1 | 9/2016 | Stapleton et al. | |
| 2016/0367336 A1 | 12/2016 | Lv et al. | |
| 2017/0100214 A1 | 4/2017 | Wen | |
| 2017/0135655 A1 | 5/2017 | Wang et al. | |
| 2017/0231721 A1 | 8/2017 | Akeel et al. | |
| 2017/0340418 A1 | 11/2017 | Raanan | |
| 2018/0028063 A1* | 2/2018 | Elbaz | G06T 17/00 |
| 2018/0028064 A1 | 2/2018 | Elbaz et al. | |
| 2018/0028065 A1 | 2/2018 | Elbaz et al. | |
| 2018/0055600 A1 | 3/2018 | Matov et al. | |
| 2018/0132982 A1 | 5/2018 | Nikolskiy et al. | |
| 2018/0146934 A1 | 5/2018 | Ripoche et al. | |
| 2018/0165818 A1 | 6/2018 | Tsai et al. | |
| 2018/0189420 A1 | 7/2018 | Fisker | |
| 2018/0303581 A1 | 10/2018 | Martz et al. | |
| 2020/0121429 A1 | 4/2020 | Pesach et al. | |

FOREIGN PATENT DOCUMENTS

| | | |
|---|---|---|
| EP | 2345387 A2 | 7/2011 |
| EP | 2886077 A1 | 6/2015 |
| WO | 3180761 A2 | 11/2001 |
| WO | 2001080763 A2 | 11/2001 |
| WO | 2013180423 A1 | 5/2013 |
| WO | 2016097033 A1 | 6/2016 |
| WO | 2017178908 A1 | 10/2017 |
| WO | 2018022054 A1 | 2/2018 |
| WO | 2018038748 A1 | 3/2018 |
| WO | 2018101923 A1 | 6/2018 |

OTHER PUBLICATIONS

Kilic et al. "GPU Supported Haptic Device Integrated Dental Simulation Environment" (Year: 2006).*
Zeng et al. "Finite Difference Error Analysis of Geometry Properties of Implicit Surfaces" (Year: 2011).*
Ibraheem, "Reduction of artifacts in dental cone beam CT images to improve the three dimensional image reconstruction" (Year: 2012).*
Changhwan Kim, Scientific Reports, "Efficient digitalization method for dental restorations using micro-CT data", www.nature.com/scientificreports, 7:44577|DOI:10.1038/srep44577 (dated Mar. 15, 2017).
Emiliano Perez et al., A Comparison of Hole-Filing Methods In 3D, Int. J. Appl. Math. Comput. Sci., 2016, vol. 26, No. 4, 885-903, in 19 pages.
Yokesh Kumar et al., Automatic Feature Identification in Dental Meshes, ResearchGate, Article in Computer-Aided Design and Applications, Aug. 2013, in 24 pages.
Andrew W. Fitzgibbon et al., Direct Least Squares Fitting of Ellipses, Department of Artificial Intelligence, The University of Edinburgh, dated Jan. 4, 1996, in 15 pages.
Oscar Sebio Cajaraville, Four Ways to Create a Mesh for a Sphere, Dec. 7, 2015, in 9 pages.
Shuai Yang et al., Interactive Tooth Segmentation Method of Dental Model based on Geodesic, ResearchGate, Conference paper, Jan. 2017, in 6 pages.
Changhwan Kim et al., Efficient digitalization method for dental restorations using micro-CT data, nature.com/scientificreports, published Mar. 15, 2017, in 8 pages.
Dexter C. Kozen, The Design and Analysis of Algorithms, Texts and Monographs in Computer Science, (c) 1992, See Whole book.
Bob Sedgewick et al., Algorithms and Data Structures Fall 2007, Department of Computer Science, Princeton University, https://www.cs.princeton.edu/~rs/AlgsDS07/, downloaded Oct. 28, 2021, in 41 pages.
Alban Pages et al., Generation of Computational Meshes from MRI and CT-Scan data, ResearchGate, ESAIM Proceedings, Sep. 2005, vol. 14, 213-223 in 12 pages.
William E. Lorensen et al., Marching Cubes: A High Resolution 3D Surface Construction Algorithm, Computer Graphics, vol. 21, No. 4, Jul. 1987 in 7 pages.
Alfred V. Aho et al., The Design and Analysis of Computer Algorithms, Addison-Wesley Publishing Company, Jun. 1974, pp. 124-155.
Sheng-hui Liao et al., Automatic Tooth Segmentation of Dental Mesh Based on Harmonic Fields, Hindawi Publishing Corporation, BioMed Research International, vol. 2015, Article ID 187173, in 11 pages.
Bribiesca, E. "3D-Curve Representation by Means of a Binary Chain Code", Mathematical and computer modelling 10.3(2004):285-295; p. 292, paragraph 2; p. 293, paragraph 1.

(56) References Cited

OTHER PUBLICATIONS

Kiattisin, S. et al. "A Match of X-Ray Teeth Films Using Image Processing Based on Special Features of Teeth", SICE Annual Conference, 2008. IEEE: Aug. 22, 2008; p. 97; col. 2, paragraph 2; a 98, col. 1-2.
Cui, M, Femiani, J., Hu, J., Wondka, Razada A. "Curve Matching for Open 2D Curves", Pattern Recognition Letters 30 (2009): pp. 1-10.
Gumhold, S., Wang, X., MacLeod R. "Feature Extraction From Point Clouds", Scientific Computing and Imaging Institute: pp. 1-13 Proceedings, 10th International Meshing Roundtable, Sandia National Laboratores, pp. 293-305, Oct. 7-10, 2001.
Wolfson, H. "On Curve Matching", Robotics Research Technical Report, Technical Report No. 256, Robotic Report No. 86 (Nov. 1986) New York University, Dept, of Computer Science, New York, New York 10012.
Rietzel et al., "Moving targets: detection and tracking of internal organ motion for treatment planning and patient set up", Radiotherapy and Oncology, vol. 73, supplement 2, Dec. 2004, pp. S68-S72.
Murat Arikan et al., O-Snap: Optimization-Based Snapping for Modeling Architecture, ACM Transactions on Grphics, vol. 32, No. 1, Article 6, Publication date: Jan. 2013, in 15 pages.
Brian Amberg et al., Optimal Step Nonrigid ICP Algorithms for Surface Registration, Proceedings/CVPR, IEEE Computer Society Conference on Computer Vision and Pattern Recognition, IEEE Computer Society Conference on Computer Vision and Pattern Recognition, Jun. 2007, in 9 pages.
T. Rabbani et al., Segmentation Of Point Clouds Using Smoothness Constraint, ISPRS vol. XXXVI, Part 5, Dresden Sep. 25-27, 2006, in 6 pages.

\* cited by examiner

SCANNING DENTAL IMPRESSIONS

CROSS-REFERENCE TO RELATED APPLICATIONS

This application claims priority to and the benefit of U.S. provisional patent application No. 62/423,460, filed Nov. 17, 2016 which is hereby incorporated by reference in its entirety.

FIELD

The present disclosure relates to systems and methods of scanning a dental impression to obtain a digital model of a patient's dentition as an input to computer aided design (CAD) and computer aided manufacturing (CAM) methods for producing dental prostheses.

BACKGROUND

Dental prostheses are typically manufactured at specialized dental laboratories that employ computer-aided design (CAD) and computer-aided manufacturing (CAM) milling systems to produce dental prostheses according to patient-specific specifications provided by dentists. In a typical work flow, information about the oral situation of a patient is received from a dentist, the dental laboratory designs the dental prosthesis, and the prosthesis is manufactured using a mill or other fabrication system. When making use of CAD design and CAM manufacturing in dentistry, a digital model of the patient's dentition is required as an input to the process. Despite the rise of intraoral scanning technology, the prevalent method of acquisition of digital model data is still scanning a stone model cast from an impression. Even in more technically advanced markets it is estimated that only 10% of clinicians own an intraoral scanner, therefore any improvements to the conventional process are likely to remain relevant and benefit patients and clinicians alike for some time. Accordingly, improvements to methods of acquiring digital models of patients' dentition are desirable.

SUMMARY

Certain embodiments of the disclosure concern systems and methods for scanning a physical impression of a patient's dentition and constructing a virtual surface image of the patient's dentition from the scan data thereby obtained. In some embodiments, the virtual surface image of the patient's dentition is constructed using isosurfaces and density gradients of a volumetric image and then directly creating a surface image based upon void spaces that correspond to the patient's dentition. This avoids an unnecessary step of first creating a surface image of the impression and then digitally or virtually reversing the surface image of the impression to obtain a surface image intended to correspond with the patient's dentition. Instead, the isosurfaces and vector gradients are selected and oriented directly to define the patient's dentition, thereby providing a surface image that is suitable for use in a dental restoration design program.

In some embodiments, the physical impression of a patient's dentition comprises a three-way dental impression tray that is adapted to obtain a physical impression containing information relating to a patient's upper jaw, lower jaw, and bite registration for at least a portion of the patient's dentition. In some embodiments, a three-way dental impression tray is scanned and the data from a single scan is used to generate virtual models of at least a portion of the patient's upper jaw, lower jaw, and bite registration. The virtual models thereby obtained are suitable for use in designing a dental restoration using known digital design products.

The foregoing and other objects, features, and advantages of the disclosed embodiments will become more apparent from the following detailed description, which proceeds with reference to the accompanying figures.

DETAILED DESCRIPTION

Figure 1:
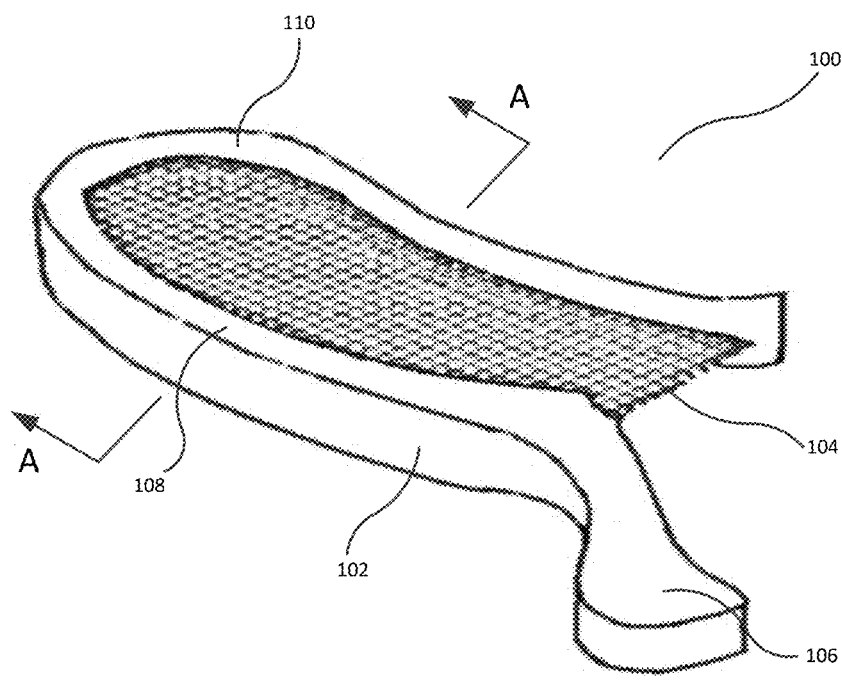
FIG. 1 is a perspective view of a three-way dental impression tray.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods. Additionally, the description sometimes uses terms like "provide" or "achieve" to describe the disclosed methods. These terms are high-level abstractions of the actual operations that are performed. The actual operations that correspond to these terms may vary depending on the particular implementation and are readily discernible by one of ordinary skill in the art.

As used in this application and in the claims, the singular forms "a," "an," and "the" include the plural forms unless the context clearly dictates otherwise. Additionally, the term "includes" means "comprises." Further, the terms "coupled" and "associated" generally mean electrically, electromagnetically, and/or physically (e.g., mechanically or chemically) coupled or linked and does not exclude the presence of intermediate elements between the coupled or associated items absent specific contrary language.

In some examples, values, procedures, or apparatus may be referred to as "lowest," "best," "minimum," or the like. It will be appreciated that such descriptions are intended to indicate that a selection among many alternatives can be made, and such selections need not be better, smaller, or otherwise preferable to other selections.

In the following description, certain terms may be used such as "up," "down," "upper," "lower," "horizontal," "vertical," "left," "right," and the like. These terms are used, where applicable, to provide some clarity of description when dealing with relative relationships. But, these terms are not intended to imply absolute relationships, positions, and/or orientations. For example, with respect to an object, an "upper" surface can become a "lower" surface simply by turning the object over. Nevertheless, it is still the same object.

As noted above, in a typical work flow, information about the oral situation of a patient is received from a dentist, the dental laboratory designs the dental prosthesis, and the prosthesis is manufactured using a mill or other fabrication system. When making use of CAD design and CAM manufacturing in dentistry, a digital model of the patient's dentition is required as an input to the process. Despite the rise of intraoral scanning technology, the prevalent method of acquisition of digital model data is still scanning a stone model cast from a physical negative impression of the patient's dentition.

A physical negative impression of the patient's dentition is typically obtained by the use of a dental impression tray containing impression material. An example of an impression tray is shown in FIG. 1 in the form of a three-way impression tray or "triple tray" 100. The triple tray 100 includes a generally rigid frame 102 within which a mesh 104 is retained. The rigid frame defines a handle 106 configured to be gripped by the user, a buccal side wall 108, and a lingual side wall 110. In use, impression material is loaded onto the upper and lower surfaces of the mesh 104 by the clinician. The triple tray 100 is then inserted into the mouth of a patient and the patient is instructed to bite down onto the triple tray 100 and impression material, causing the impression material to conform to the patient's dentition as the impression material cures. Because the triple tray 100 is situated between the upper and lower jaws of the patient, the impression obtained via the triple tray 100 includes information about the dental situation of the patient's upper jaw, lower jaw, and bite registration in the area of the patient's dentition covered by the triple tray.

Figure 2:
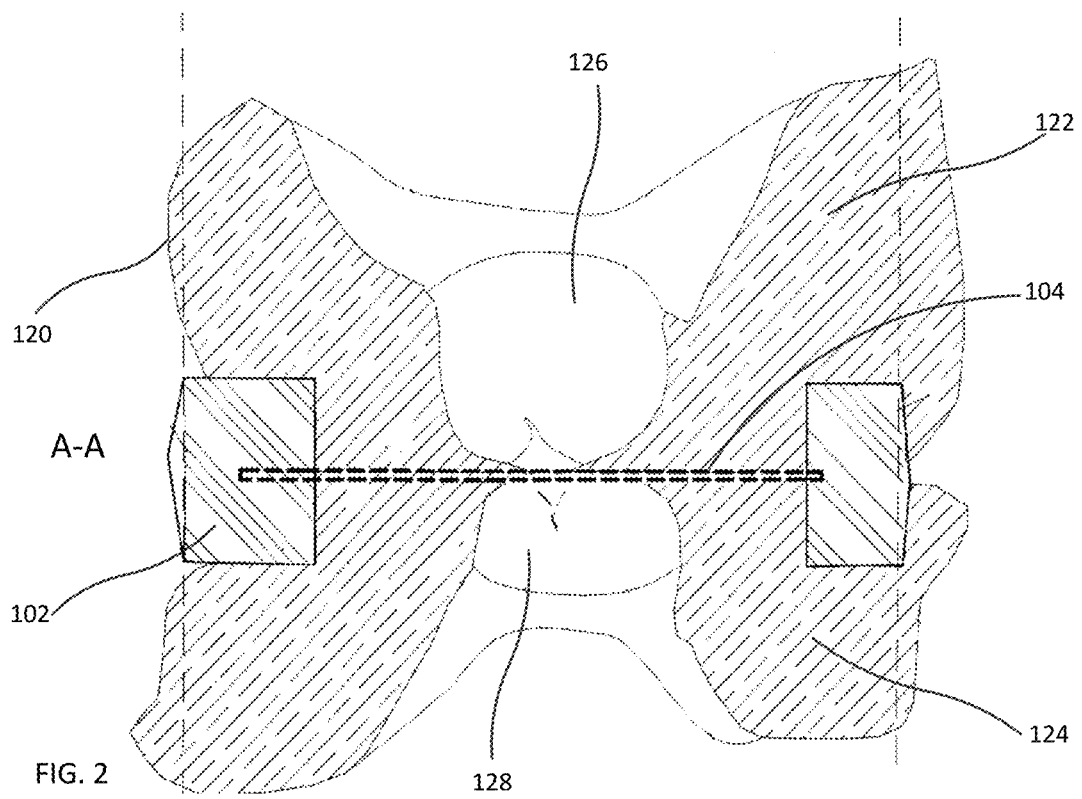
FIG. 2 is a cross-sectional view of a three-way dental impression tray containing impression material.

For example, in FIG. 2, there is shown a sectional view of the triple tray 100 containing impression material 120 after the taking of a physical impression of a patient. An upper impression 122 is formed on the upper side of the mesh 104, and a lower impression 124 is formed on the lower side of the mesh 104. As noted above, after deformation, the impression material 122 defines a physical negative impression of the patient's dentition. Accordingly, the upper void space 126 defined by the upper impression 122 defines the space occupied by the patient's teeth and gingiva in the patient's upper jaw, and the lower void space 128 defined by the lower impression 124 defines the space occupied by the patient's teeth and gingiva in the patient's lower jaw. Moreover, the location and orientation of the upper void space 126 relative to the lower void space 128 defines the bite registration of the patient's dentition in the subject area, including the occlusal spacing and registration.

As noted above, in a conventional workflow, a physical dental impression formed in the manner described above would be used to cast a model of the patient's dentition formed of stone, polymeric, or other suitable material. The cast model would then be scanned using a laser scanner in order to obtain a digital model. The digital model would then be used to design one or more restorations, or for other purposes. This conventional workflow creates potential sources of error or inaccuracy that would be avoided by alternative methods or alternative workflows that avoided the step of forming the case model and, instead, proceeded directly from the physical impression to a digital model.

Figure 3:
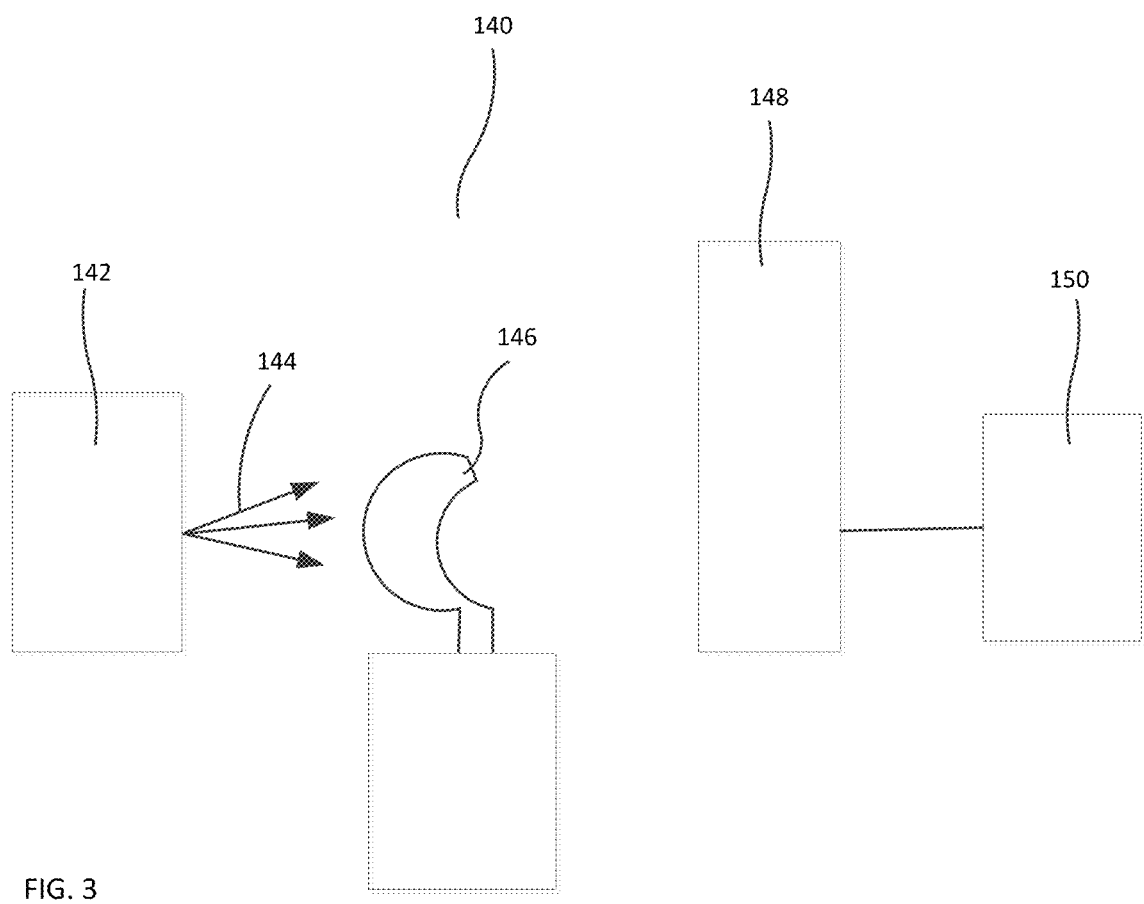
FIG. 3 is a schematic diagram of a computed tomography (CT) scanning system.

In one embodiment of the present method, a computed tomography (CT) scanner uses x-rays to make a detailed image of a physical impression. A plurality of such images are then combined to form a 3D model of the patient's dentition. A schematic diagram of an example of a CT scanning system 140 is shown in FIG. 3. The CT scanning system 140 includes a source of x-ray radiation 142 that emits an x-ray beam 144. An object being scanned—in the present case, a triple tray containing a physical impression 146—is placed between the source 142 and an x-ray detector 148. The x-ray detector 148, in turn, is connected to a processor 150 that is configured to receive the information from the detector 148 and to convert the information into a digital image file. Those skilled in the art will recognize that the processor 150 may comprise one or more computers that may be directly connected to the detector, wirelessly connected, connected via a network, or otherwise in direct or indirect communication with the detector 148.

An example of a suitable scanning system 140 includes a Nikon Model XTH 255 CT Scanner which is commercially available from Nikon Corporation. The example scanning system includes a 225 kV microfocus x-ray source with a 3 µm focal spot size to provide high performance image acquisition and volume processing. The processor 150 may include a storage medium that is configured with instructions to manage the data collected by the scanning system.

Figure 4:
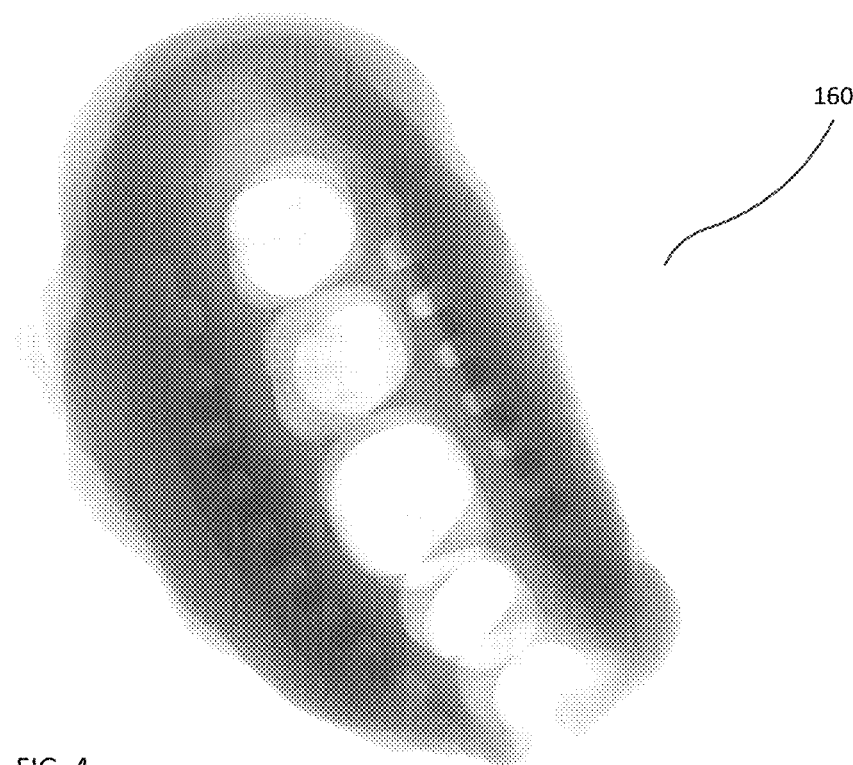
FIG. 4 is a 2-dimensional (2D) radiographic image of a dental impression tray containing a dental impression.

As noted above, during operation of the scanning system 140, the impression 146 is located between the x-ray source 142 and the x-ray detector 148. A series of images of the impression 146 are collected by the processor 150 as the impression 146 is rotated in place between the source 142 and the detector 146. An example of a single image 160 is shown in FIG. 4. The image 160 may be a radiograph, a projection, or other form of digital image. In one embodiment, a series of 720 images are collected as the impression 146 is rotated in place between the source 142 and the detector 148. In other embodiments, more images or fewer images may be collected as will be understood by those skilled in the art.

Figure 5:
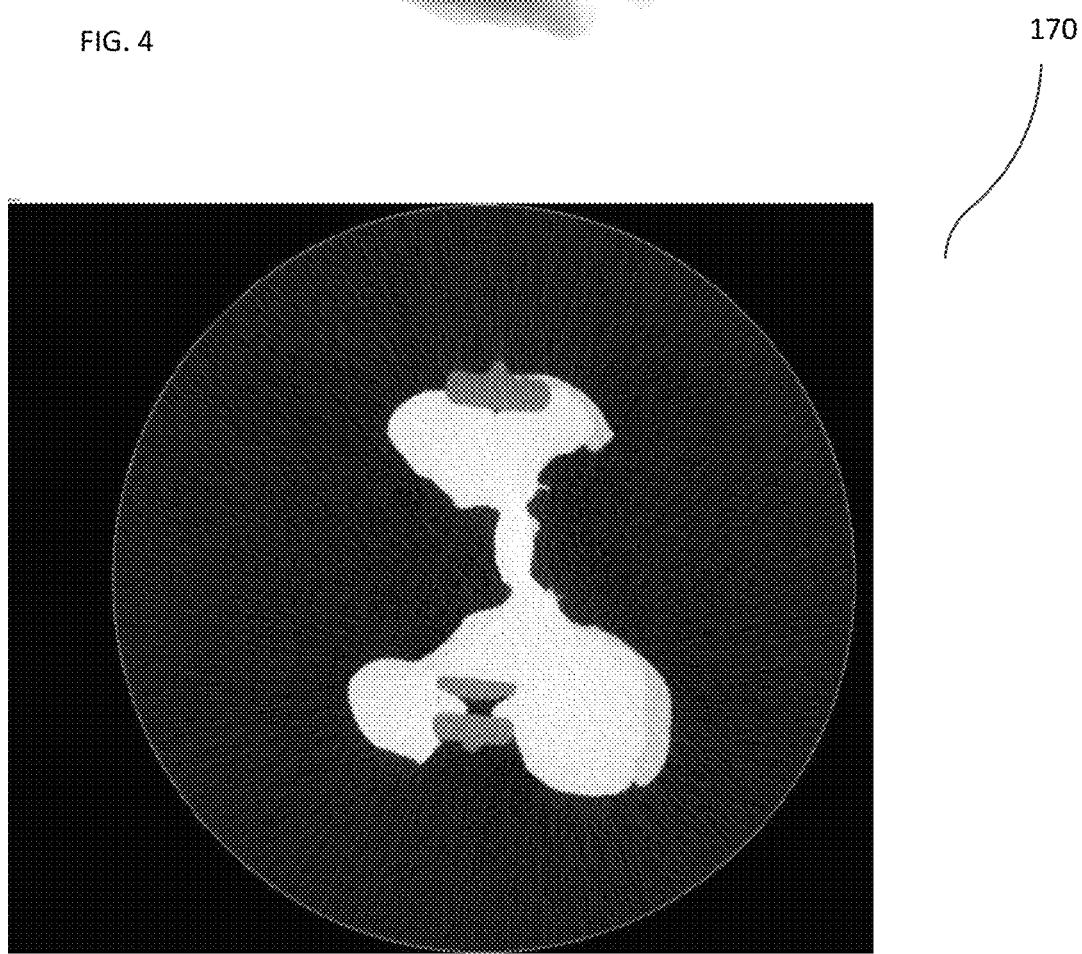
FIG. 5 is a cross-section of a 3-dimensional (3D) volumetric image.

The plurality of images 160 of the impression 146 are generated by and stored within a storage medium contained within the processor 150 of the scanning system 140, where they may be used by software contained within the processor to perform additional operations. For example, in an embodiment, the plurality of images 160 undergo tomographic reconstruction in order to generate a 3D virtual image 170 (see FIG. 5) from the plurality of 2D images 160 generated by the scanning system 140. In the embodiment shown in FIG. 5, the 3D virtual image 170 is in the form of a volumetric image or volumetric density file (shown in cross-section in FIG. 5) that is generated from the plurality of radiographs 160 by way of a reconstruction algorithm associated with the scanning system 140.

Figure 6:
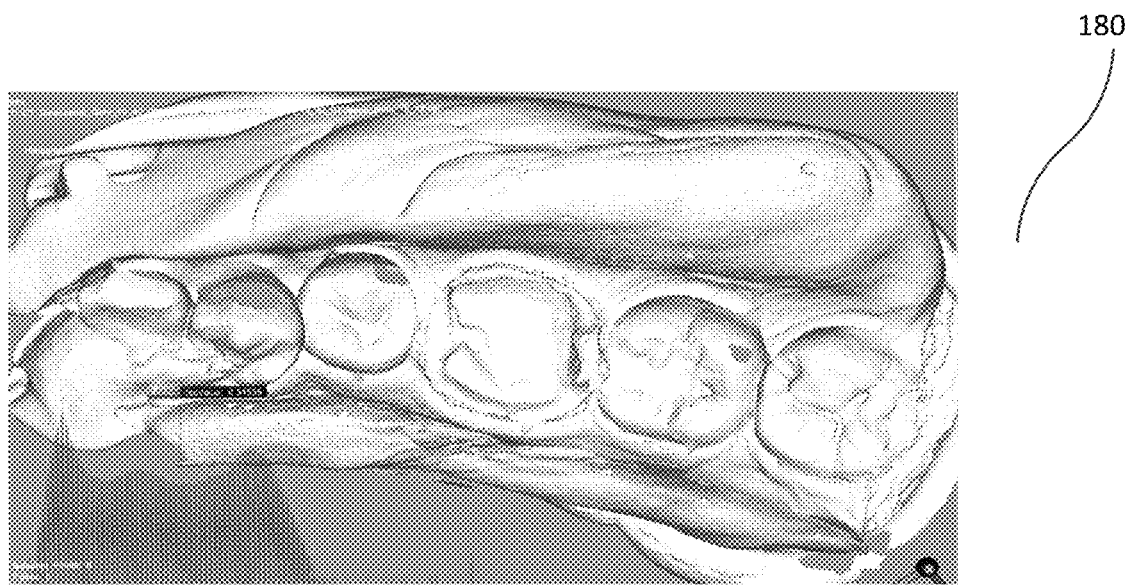
FIG. 6 is a 3-dimensional (3D) surface image representation of a portion of a patient's dentition.

In one embodiment, the volumetric image 170 is converted into a surface image 180 (see, e.g., FIG. 6) using a surface imaging algorithm. In the embodiment shown, the volumetric image 170 is converted into a surface image 180 having a format (e.g., an .STL file format) that is suitable for use with a dental restoration design software, such as the FastDesign™ dental design software provided by Glidewell Laboratories of Newport Beach, Calif.

Figure 7:
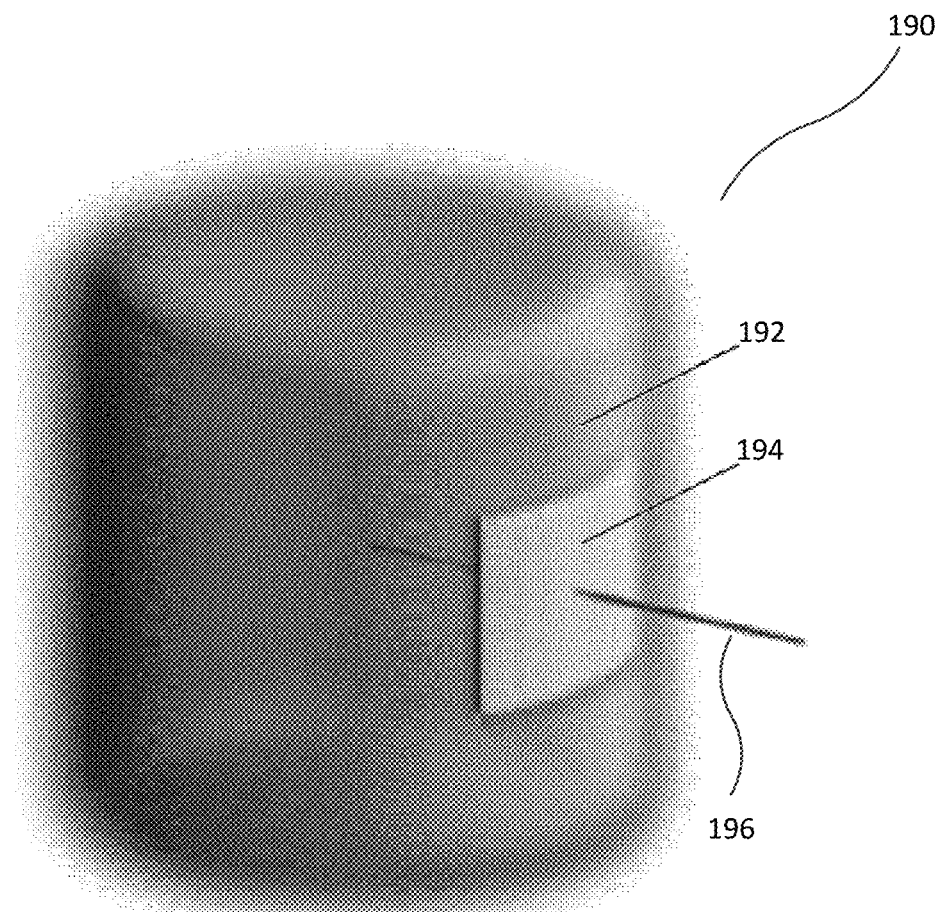
FIG. 7 is an illustration of a 3-dimensional (3D) object in the form of a cylinder.
Figure 8A:
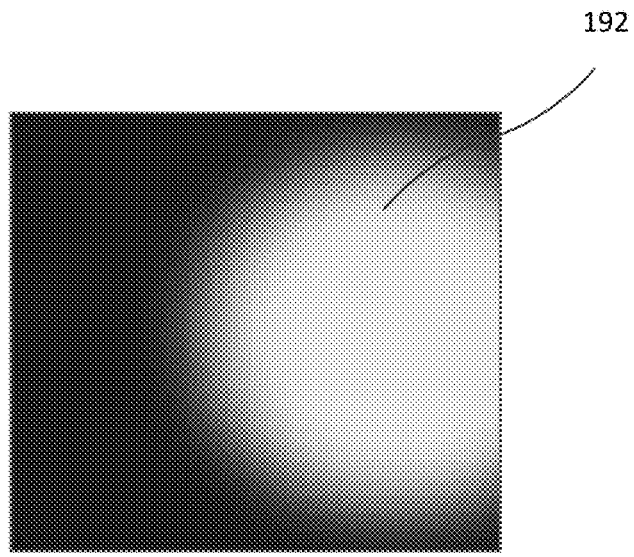
FIG. 8A is an illustration of a cross-section of the cylinder of FIG. 7.
Figure 8B:
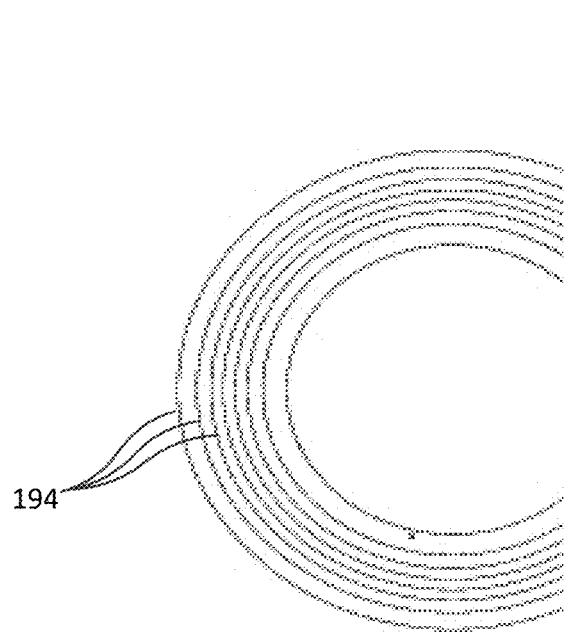
FIG. 8B is an illustration of isosurfaces derived from the 3D image of the cylinder of FIG. 7.
Figure 8C:
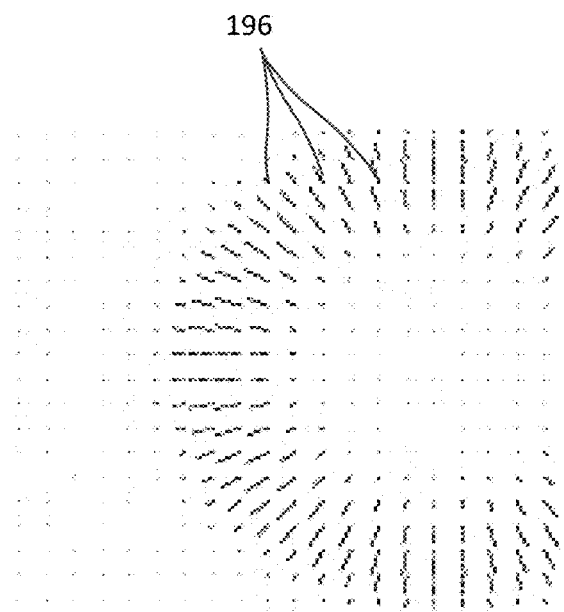
FIG. 8C is an illustration of gradient vectors derived from the isosurfaces shown in FIG. 8B.

In one embodiment, the surface imaging algorithm used to convert the volumetric image 170 into a surface image 180 is configured to construct the surface image of the dentition 180 directly from the volumetric image 170 without including an intermediate step of constructing a surface image of the impression. For example, FIGS. 7 and 8A-C do not show images of a dental impression or of a patient's dentition, but are instead presented to illustrate by way of example the direct surface imaging method employed in the illustrated embodiment. In FIG. 7, a volumetric image 190 of an object having a boundary 192 that is not precisely defined. A small patch of an isosurface 194 is illustrated within the boundary 192, with the isosurface 194 representing a collection of points within the volumetric image 190 that have the same volumetric density value. It is a mathematical property that a gradient vector 196 at a given position will always point perpendicular to an isosurface 194 at position. Accordingly, the gradient vector 196 is used to determine the direction which passes perpendicularly through the object boundary 192. These properties are further illustrated in FIGS. 8A-C, which show the non-precisely defined boundary 192 of the object (FIG. 8A), a plurality of isosurfaces 194 of the object (FIG. 8B), and a plurality of gradient vectors 196 that are perpendicular to the isosurfaces at given positions with in the object (FIG. 8C).

In one embodiment, the surface imaging algorithm used to convert the volumetric image 170 of the dental impression into a surface image 180 of the patient's dentition relies on defining isosurfaces and density gradients and then directly creating a surface image based upon the void spaces 126 and 128 (see, e.g., FIG. 2) that correspond to the patient's dentition. This avoids an unnecessary step of first creating a surface image of the impression 122, 124 and then digitally or virtually reversing the surface image of the impression to obtain a surface image intended to correspond with the patient's dentition. Instead, the isosurfaces and vector gradients are selected and oriented directly to define the patient's dentition, thereby providing a surface image 180 that is suitable for use in a dental restoration design program.

In the embodiment shown, as described above, a dental impression is collected using a triple tray 100 dental impression tray, thereby collecting an upper impression 122, a lower impression 124, and a bite registration in a single step. As a result, after scanning, reconstruction, and generation of a volumetric image of the triple tray and impression 146 (see FIG. 3), the resulting surface image 200 (see FIG. 9) includes a surface image of the upper dentition 202, a surface image of the lower dentition 204, and their relative positions and orientation providing information about the bite registration between the upper and lower dentition. These surface images 202, 204 and bite registration information are obtained using a single scan of a single object (the triple tray and impression 146).

Figure 9:
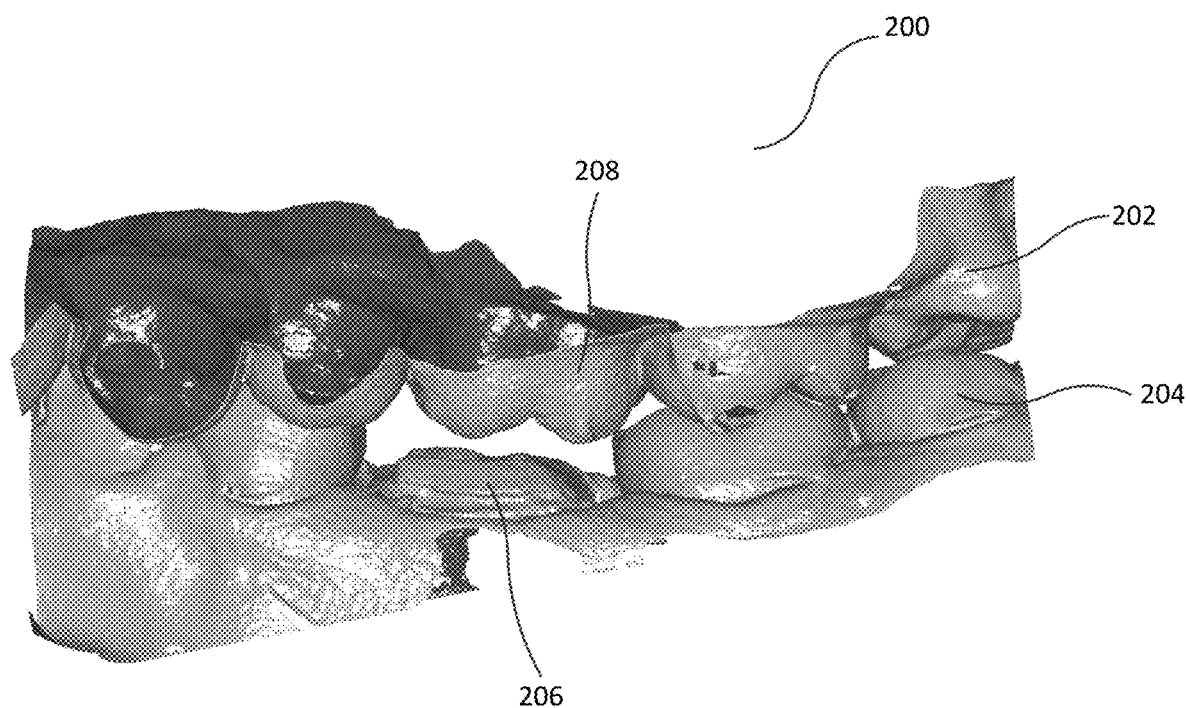
FIG. 9 is a perspective view of a surface image representation of a portion of a patient's dentition including portions of the dentition of an upper jaw and portions of the dentition of a lower jaw.
Figure 10:
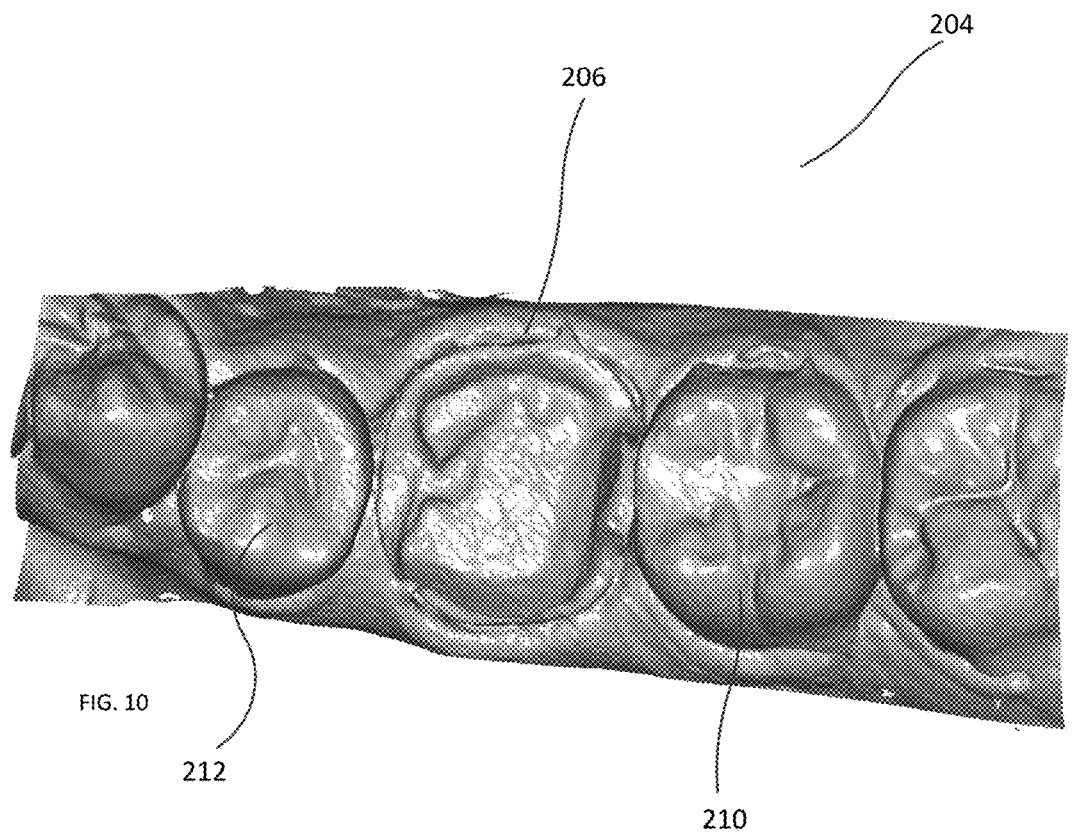
FIG. 10 is an overhead view of the surface image representation of the lower jaw dentition shown in FIG. 9.

For example, in FIG. 9, the surface image of the lower dentition 204 includes a representation of the tooth preparation 206 (i.e., the tooth that has been prepared by the dentist for a restoration to be designed using the surface image). The surface image of the upper dentition 202 includes a representation of the opposing tooth 208 (i.e., the tooth or teeth that are in the opposite jaw from the jaw containing the tooth preparation 206 and that are in opposition to the tooth preparation 204 when the jaws are closed in a bite). The orientation and relative positions of the teeth in the lower jaw and upper jaw, including the tooth preparation 206 and the opposing tooth 208, provide the bite registration. The bite registration information is used by the dental restoration design software to determine, for example, limitations on the height, shape, and position of the occlusal surface of the restoration being designed. Additional information is provided by the size, shape, and positions of the teeth 210 and 212 adjacent to the tooth preparation 206, as shown in FIG. 10.

The above descriptions of the scanning system and the algorithms used to perform the scanning, imaging, reconstruction, and surface imaging functions are not intended to suggest any limitation as to scope of use or functionality, as the innovations may be implemented in diverse general-purpose or special-purpose computing systems. For example, the computing environment used to perform these functions can be any of a variety of computing devices (e.g., desktop computer, laptop computer, server computer, tablet computer, gaming system, mobile device, programmable automation controller, etc.) that can be incorporated into a computing system comprising one or more computing devices.

For example, a computing environment may include one or more processing units and memory. The processing units execute computer-executable instructions. A processing unit can be a central processing unit (CPU), a processor in an application-specific integrated circuit (ASIC), or any other type of processor. In a multi-processing system, multiple processing units execute computer-executable instructions to increase processing power. For example, a representative computing environment may include a central processing unit as well as a graphics processing unit or co-processing unit. The tangible memory may be volatile memory (e.g., registers, cache, RAM), non-volatile memory (e.g., ROM, EEPROM, flash memory, etc.), or some combination of the two, accessible by the processing unit(s). The memory stores software implementing one or more innovations described herein, in the form of computer-executable instructions suitable for execution by the processing unit(s).

A computing system may have additional features. For example, in some embodiments, the computing environment includes storage, one or more input devices, one or more output devices, and one or more communication connections. An interconnection mechanism such as a bus, controller, or network, interconnects the components of the computing environment. Typically, operating system software provides an operating environment for other software executing in the computing environment, and coordinates activities of the components of the computing environment.

The tangible storage may be removable or non-removable, and includes magnetic or optical media such as magnetic disks, magnetic tapes or cassettes, CD-ROMs, DVDs, or any other medium that can be used to store information in a non-transitory way and can be accessed within the computing environment. The storage stores instructions for the software implementing one or more innovations described herein.

The input device(s) may be, for example: a touch input device, such as a keyboard, mouse, pen, or trackball; a voice input device; a scanning device; any of various sensors; another device that provides input to the computing environment; or combinations thereof. For video encoding, the input device(s) may be a camera, video card, TV tuner card, or similar device that accepts video input in analog or digital form, or a CD-ROM or CD-RW that reads video samples into the computing environment. The output device(s) may be a display, printer, speaker, CD-writer, or another device that provides output from the computing environment.

The communication connection(s) enable communication over a communication medium to another computing entity. The communication medium conveys information, such as computer-executable instructions, audio or video input or output, or other data in a modulated data signal. A modulated data signal is a signal that has one or more of its characteristics set or changed in such a manner as to encode information in the signal. By way of example, and not limitation, communication media can use an electrical, optical, RF, or other carrier.

Any of the disclosed methods can be implemented as computer-executable instructions stored on one or more computer-readable storage media (e.g., one or more optical media discs, volatile memory components (such as DRAM or SRAM), or nonvolatile memory components (such as flash memory or hard drives)) and executed on a computer (e.g., any commercially available computer, including smart phones, other mobile devices that include computing hardware, or programmable automation controllers) (e.g., the computer-executable instructions cause one or more processors of a computer system to perform the method). The term computer-readable storage media does not include communication connections, such as signals and carrier waves. Any of the computer-executable instructions for implementing the disclosed techniques as well as any data created and used during implementation of the disclosed embodiments can be stored on one or more computer-readable storage media. The computer-executable instructions can be part of, for example, a dedicated software application or a software application that is accessed or downloaded via a web browser or other software application (such as a remote computing application). Such software can be executed, for example, on a single local computer (e.g., any suitable commercially available computer) or in a network environment (e.g., via the Internet, a wide-area network, a local-area network, a client-server network (such as a cloud computing network), or other such network) using one or more network computers.

For clarity, only certain selected aspects of the software-based implementations are described. Other details that are well known in the art are omitted. For example, it should be understood that the disclosed technology is not limited to any specific computer language or program. For instance, the disclosed technology can be implemented by software written in C++, Java, Perl, Python, JavaScript, Adobe Flash, or any other suitable programming language. Likewise, the disclosed technology is not limited to any particular computer or type of hardware. Certain details of suitable computers and hardware are well known and need not be set forth in detail in this disclosure.

It should also be well understood that any functionality described herein can be performed, at least in part, by one or more hardware logic components, instead of software. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

Furthermore, any of the software-based embodiments (comprising, for example, computer-executable instructions for causing a computer to perform any of the disclosed methods) can be uploaded, downloaded, or remotely accessed through a suitable communication means. Such suitable communication means include, for example, the Internet, the World Wide Web, an intranet, software applications, cable (including fiber optic cable), magnetic communications, electromagnetic communications (including RF, microwave, and infrared communications), electronic communications, or other such communication means.

In view of the many possible embodiments to which the principles of the disclosure may be applied, it should be recognized that the illustrated embodiments are only preferred examples and should not be taken as limiting the scope of the disclosure. Rather, the scope of the invention is defined by all that comes within the scope and spirit of the following claims.

What is claimed is:

1. A computer-implemented method of designing a dental restoration for a patient, comprising:
   providing a physical negative impression of at least a portion of the patient's dentition, the physical negative impression comprising an impression tray containing impression material previously molded to the at least a portion of the patient's dentition;
   using a computed tomography (CT) scanner system, scanning the physical negative impression to create a three dimensional (3D) virtual image corresponding to the physical negative impression, the 3D virtual image comprising a volumetric density file;
   using the 3D virtual image of the physical negative impression, directly constructing a surface image of the at least a portion of the patient's dentition from the 3D virtual image of the physical negative impression without constructing a surface image of the physical negative impression; and
   designing a dental restoration for the patient based upon the surface image of the at least a portion of the patient's dentition,
   wherein the step of directly constructing a surface image of the at least a portion of the patient's dentition from the 3D virtual image of the physical negative impression further includes:
   defining isosurfaces having the same volumetric density value within the 3D virtual image; and
   identifying density gradient vectors from the defined isosurfaces.

2. The computer-implemented method of claim 1, wherein the CT scanner system includes a source of x-ray radiation, an x-ray detector, and a processor connected to the detector, and wherein the step of scanning the physical negative impression further includes:
   locating the physical negative impression between the source of x-ray radiation and the x-ray detector; and
   rotating the physical negative impression in place as a series of images is captured by the CT scanner system.

3. The computer-implemented method of claim 2, further including a step of reconstructing the series of images to create the 3D virtual image.

4. The computer-implemented method of claim 1, wherein the step of directly constructing a surface image further includes constructing a surface image that corresponds with void spaces of the physical negative impression.

5. The computer-implemented method of claim 4, wherein the surface image includes an upper dentition surface image, a lower dentition surface image, and bite registration information between the upper dentition and lower dentition.

6. The computer-implemented method of claim 5, wherein the surface image is in .STL file format.

7. A system for designing a dental restoration for a patient, the system comprising:
- a source of x-ray radiation;
- an x-ray detector;
- a processor; and
- a non-transitory computer-readable storage medium comprising instructions executable by the processor to perform steps comprising:
  - reconstructing a series of two dimensional (2D) images collected by the x-ray detector to create a three dimensional (3D) virtual image comprising a volumetric density file corresponding to a physical negative impression of at least a portion of the patient's dentition;
  - using the 3D virtual image of the physical negative impression, directly constructing a surface image of the at least a portion of the patient's dentition from the 3D virtual image of the physical negative impression without constructing a surface image of the physical negative impression; and
  - designing a dental restoration for the patient based upon the surface image of the at least a portion of the patient's dentition,
  - wherein the step of directly constructing a surface image of the at least a portion of the patient's dentition from the 3D virtual image of the physical negative impression further comprises:
  - defining isosurfaces having the same volumetric density value within the 3D virtual image; and
  - identifying density gradient vectors from the defined isosurfaces.

8. The system of claim 7, wherein the step of directly constructing a surface image further includes constructing a surface image that corresponds with void spaces of the physical negative impression.

9. The system of claim 8, wherein the surface image includes an upper dentition surface image, a lower dentition surface image, and bite registration information between the upper dentition and lower dentition.

10. The system of claim 9, wherein the surface image is in .STL file format.

* * * * *